(12) United States Patent
Bettarini et al.

(10) Patent No.: US 8,252,721 B2
(45) Date of Patent: Aug. 28, 2012

(54) HERBICIDAL COMPOSITIONS

(75) Inventors: Franco Bettarini, Rapallo (IT); Luca Fornara, Vasto (IT); Mauro Vanzulli, Saronno (IT)

(73) Assignee: ISEM S.r.l., Milan (IT)

( * ) Notice: Subject to any disclaimer, the term of this patent is extended or adjusted under 35 U.S.C. 154(b) by 346 days.

(21) Appl. No.: 12/518,499

(22) PCT Filed: Dec. 5, 2007

(86) PCT No.: PCT/EP2007/010764
§ 371 (c)(1),
(2), (4) Date: Jul. 7, 2009

(87) PCT Pub. No.: WO2008/071377
PCT Pub. Date: Jun. 19, 2008

(65) Prior Publication Data
US 2010/0016160 A1    Jan. 21, 2010

(30) Foreign Application Priority Data

Dec. 11, 2006 (IT) .............................. MI2006A2368

(51) Int. Cl.
*A01N 43/60* (2006.01)
(52) U.S. Cl. ...................................... 504/136
(58) Field of Classification Search .................. None
See application file for complete search history.

(56) References Cited

U.S. PATENT DOCUMENTS

| | | | | |
|---|---|---|---|---|
| 6,329,323 B1 * | 12/2001 | Bettarini et al. | ............ | 504/214 |
| 2006/0183637 A1 * | 8/2006 | Loughner et al. | ............ | 504/101 |
| 2006/0276341 A1 * | 12/2006 | Zagar et al. | ............ | 504/167 |
| 2006/0287199 A1 * | 12/2006 | Yamashita et al. | ............ | 504/136 |

FOREIGN PATENT DOCUMENTS

| | | |
|---|---|---|
| DE | 42 09 475 | 9/1993 |
| WO | 2006 072359 | 7/2006 |

* cited by examiner

*Primary Examiner* — Johann Richter
*Assistant Examiner* — Thor Nielsen
(74) *Attorney, Agent, or Firm* — Oblon, Spivak, McClelland, Maier & Neustadt, L.L.P.

(57) ABSTRACT

A description follows of compositions with a herbicidal activity containing the compound having formula (I), mixed with one or more known herbicidal products, possibly stabilized by the addition of at least one inorganic or organic base, and the relative use for the control of weeds in agricultural crops.

(I)

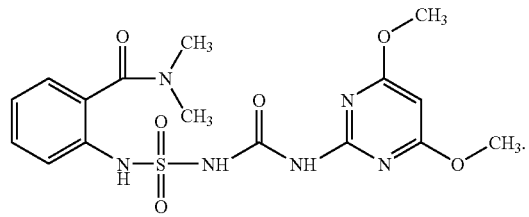

12 Claims, No Drawings

HERBICIDAL COMPOSITIONS

CROSS-REFERENCE TO RELATED APPLICATIONS

This application is a National Stage of PCT/EP07/010,764 filed Dec. 5, 2007 and claims the benefit of Italian application MI2006A002368 filed Dec. 11, 2006.

The present invention relates to herbicidal compositions.

More specifically, the present invention relates to compositions comprising a compound belonging to the group of aminosulfonylureas mixed with one or more known herbicidal products, and their use for the control of weeds in agricultural crops.

International patent application WO 98/40361 describes new aminosulfonylureas with a herbicidal activity and their use for the control of weeds in agricultural crops.

Among the preferred compounds of the above patent application the compound having the structural formula (I) is mentioned:

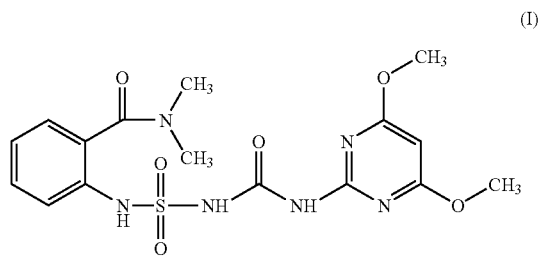

i.e. 2-[[[[[(4,6-dimethoxy-2-pyrimidinyl)amino]carbonyl]amino]sulfonyl]amino]-N—N-dimethylbenzamide, known with the ISO name orthosulfamuron (compound Nr. 1 of WO 98/40361).

The Applicant has surprisingly found that the compound having formula (I) can be associated with one or more known herbicidal products, selected from those specified hereafter, producing herbicidal mixtures having an improved herbicidal activity with respect to that expected on the basis of the activity of the products used separately.

An object of the present invention therefore relates to herbicidal compositions comprising a component [A] and a component [B], where the component [A] is the compound having formula (I)

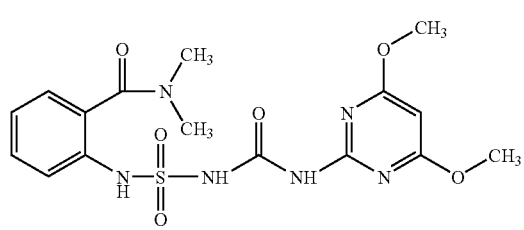

and component [B] consists of at least one product selected from the following known herbicides:
[1] propanil: N-(3,4-dichlorophenyl)propanamide;
[2] butachlor: N-(butoxymethyl)-2-chloro-N-(2,6-diethylphenyl)acetamide;
[3] pretilachlor: 2-chloro-N-(2,6-diethylphenyl)-N-(2-propoxyethyl)acetamide;
[4] acetochlor: 2-chloro-N-(ethoxymethyl)-N-(2-ethyl-6-methylphenyl)acetamide;
[5] benfuresate: 2,3-dihydro-3,3-dimethyl-5-benzofuranylethanesulfonate;
[6] benzobicyclon: 3-[2-chloro-4-(methylsulfonyl)benzoyl]-4-(phenylthio)bicyclo[3.2.1]oct-3-en-2-one;
[7] bromobutide: 2-bromo-3,3-dimethyl-N-(1-methyl-1-phenylethyl)butanamide;
[8] carfentrazone-ethyl: ethyl $\alpha$,2-dichloro-5-[4-(difluoromethyl)-4,5-dihydro-3-methyl-5-oxo-1H,1,2,4-triazol-1-yl]-4-fluorobenzenepropanoate;
[9] clomazone: 2-[(chlorophenyl)methyl]-4,4-dimethyl-3-isoxazolidinone;
[10] 2,4-D: (2,4-dichlorophenoxy)acetic acid, its esters and salts;
[11] diflufenican: N-(2,4-difluorophenyl)-2-[3-(trifluoromethyl)phenoxy]-3-pyridinecarboxamide;
[12] fentrazamide: N-cyclohexyl-N-ethyl-4-(2-chlorophenyl)-4,5-dihydro-5-oxo-1H-tetrazole-1-carboxamide;
[13] flufenacet: N-(4-fluorophenyl)-N-(1-methylethyl)-2-[[5-trifluoromethyl)-1,3,4-thiadiazol-2-yl]oxy]acetamide;
[14] imazethapyr: ($\pm$)-2-[4,5-dihydro-4-methyl-4-(1-methylethyl)-5-oxo-1H-imidazol-2-yl]-5-ethyl-3-pyridinecarboxylic acid;
[15] isoproturon: N,N-dimethyl-N'-[4-(1-methylethyl)phenyl)urea;
[16] linuron: N'(3,4-dichlorophenyl)-N-methoxy-N-methylurea;
[17] MCPA: (4-chloro-2-methylphenoxy)acetic acid, its esters and salts;
[18] MCPA-thioethyl: S-ethyl (4-chloro-2-methylphenoxy)ethanethioate;
[19] mefenacet: 2-(2-benzothiazolyloxy)-N-methyl-N-phenylacetamide;
[20] metributzin: 4-amino-6-(1,1-dimethylethyl)-3-(methylthio)-1,2,4-triazin-5(4H)-one;
[21] pendimethalin: N-(1-ethylpropyl)-3,4-dimethyl-2,6-dinitrobenzeneamine;
[22] penoxsulam: 2-(2,2-difluoroethoxy)-N-(5,8-dimethoxy-[1,2,4]triazole[1,5-c]pyrimidin-2-yl)-6-trifluoromethyl)benzenesulfonamide;
[23] picolinafen: N-(4-fluorophenyl)-6-[3-(trifluoromethyl)phenoxy]-2-pyridinecarboxamide;
[24] quinclorac: 3,7-dichloro-8-quinolinecarboxylic acid;
[25] thiobencarb: S-[(4-chlorophenyl)methyl]-diethylcarbamothioate;
[26] trifluralin: 2,6-dinitro-N,N-dipropyl-4-(trifluoromethyl)benzeneamine;
[27] ametryn: N-ethyl-N'-(1-methylethyl)-6-(methylthio)-1,3,5-triazine-2,4-diamine;
[28] asulam: methyl [(4-aminophenyl)-sulfonyl]-carbamate;
[29] atrazine: 6-chloro-N-ethyl-N'-(1-methylethyl)-1,3,5-triazine-2,4-diamine;
[30] bromoxynil: 3,5-dibromo-4-hydroxybenzonitrile, its potassium salt and its octanoic ester;
[31] clopyralid: 3,6-dichloro-2-pyridinecarboxylic acid;
[32] dicamba: 3,6-dichloro-2-methoxybenzoic acid and its salts;
[33] diuron: N'-(3,4-dichlorophenyl)-N,N-dimethyl-urea;
[34] fluoroxypyr: [(4-amino-3,5-dichloro-6-fluoro-2-pyridinyl)oxy]acetic acid and its esters;
[35] glufosinate-ammonium: ammonium ($\pm$)-2-amino-4-(hydroxymethylphosphinyl)butanoate;
[36] glyphosate: N-(phosphonomethyl)glycine and its salts;

[37] halosulfuron: 3-chloro-5-[[[[(4,6-dimethoxy-2-pyrimidinyl)amino]carboyl]amino]sulfonyl]-1-methyl-1H-pyrazole-4-carboxylic acid and its methyl ester;

[38] imazamox: 2-[4,5-dihydro-4-methyl-4-(1-methylethyl)-5-oxo-1H-imidazol-2-yl]-5-(methoxymethyl)-3-pyridinecarboxylic acid;

[39] imazapic: 2-[4,5-dihydro-4-methyl-4-(1-methylethyl)-5-oxo-1H-imidazol-2-yl]-5-methyl-3-pyridinecarboxylic acid, its salts and esters;

[40] ioxynil: 4-hydroxy-3,5-diiodobenzonitrile, its sodium salt and its octanoic ester;

[41] lactofen: (±)-2-ethoxy-1-ethyl-2-oxoethyl 5-[2-chloro-4-(trifluoromethyl)phenoxy]-2-nitrobenzoate;

[42] mesosulfuron: 2-[[[[(4,6-dimethoxy-2-pyrimidinyl)]amino]methyl]benzoic acid, its salts and esters;

[43] metolachlor: 2-chloro-N-(2-ethyl-6-methylphenyl)-N-(2-methoxy-1-methylethyl)acetamide;

[44] metsulfuron: 2-[[[[(4-methoxy-6-methyl-1,3,5-triazin-2-yl)amino]carbonyl]amino]sulfonyl]benzoic acid and its methyl ester;

[45] oxadiazon: 3-[2,4-dichloro-5-(1-methylethoxy)phenyl]-5-(1,1-dimethylethyl-1,3,4-oxadiazol-2(3H)-one;

[46] paraquat: 1,1'-dimethyl-4,4'-bipyridinium;

[47] picloram: 4-amino-3,5,6-trichloro-2-pyridinecarboxylic acid and its potassium salt;

[48] pyraflufen-ethyl: ethyl 2-chloro-5-[4-chloro-5-(difluoromethoxy)-1-methyl-1H-pyrazol-3-yl]-4-fluorophenoxyacetate;

[49] sulfentrazone: N-[2,4-dichloro-5-[4-(difluoromethyl)-4,5-dihydro-3-methyl-5-oxo-1H-1,2,4-triazol-1-yl]phenyl]methanesulfonamide;

[50] triasulfuron: 2-(2-chloroethoxy)-N-[[4-methoxy-6-methyl-1,3,5-triazin-2-yl)amino]carbonyl]benzenesulfonamide;

[51] tribenuron: 2-[[[[(4-methoxy-6-methyl-1,3,5-triazin-2-yl)methylamino]carbonyl]sulfonyl]benzoic acid and its methyl ester;

[52] triclopyr: [(3,5,6-trichloro-2-pyridinyl)oxy]-acetic acid, its esters and salts;

[53] trifloxysulfuron: N-[[(4,6-dimethoxy-2-pyrimidinyl)amino]carbonyl]-3-(2,2,2-trifluoroethoxy)-2-pyridinesulfonamide;

[54] methylarsonic acid and its monosodium (MSMA) and disodium (DMSA) salts;

[55] prometryn: N,N'-bis(1-methylethyl)-6-(methylthio)-1,3,5-triazine-2,4-diamine;

[56] simazine: 6-chloro-N,N'-diethyl-1,3,5-triazine-2,4-diamine;

[57] mecoprop: 2-(4-chloro-2-methylphenoxy)propanoic acid, its salts and esters.

In some cases, however, it has been found that said compositions have a limited chemical stability, due to the tendency of the splitting of the bonds which apply in particular to the central —NH— group of the compound having formula (I), with the consequent formation of inactive by-products and loss of the herbicidal activity of the composition over a period of time.

It has also been observed that it is possible to overcome this drawback by adding suitable quantities of at least one inorganic or organic base to the compositions.

A further object of the present invention therefore relates to herbicidal compositions comprising a component [A] and a component [B], wherein component [A] is the compound having formula (I)

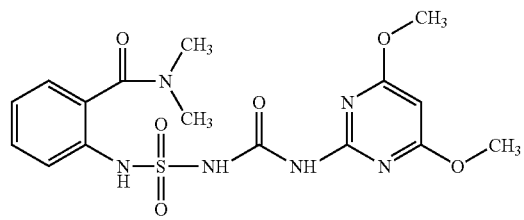

and component [B] consists of at least one product selected from the following known herbicides:

[1] propanil: N-(3,4-dichlorophenyl)propanamide;

[2] butachlor: N-(butoxymethyl)-2-chloro-N-(2,6-diethylphenyl)acetamide;

[3] pretilachlor: 2-chloro-N-(2,6-diethylphenyl)-N-(2-propoxyethyl)acetamide;

[4] acetochlor: 2-chloro-N-(ethoxymethyl)-N-(2-ethyl-6-methylphenyl)acetamide;

[5] benfuresate: 2,3-dihydro-3,3-dimethyl-5-benzofuranylethanesulfonate;

[6] benzobicyclon: 3-[2-chloro-4-(methylsulfonyl)benzoyl]-4-(phenylthio)bicyclo[3.2.1]oct-3-en-2-one;

[7] bromobutide: 2-bromo-3,3-dimethyl-N-(1-methyl-1-phenylethyl)butaneamide;

[8] carfentrazone-ethyl: ethyl α,2-dichloro-5-[4-(difluoromethyl)-4,5-dihydro-3-methyl-5-oxo-1H,1,2,4-triazol-1-yl]-4-fluorobenzenepropanoate;

[9] clomazone: 2-[(chlorophenyl)methyl]-4,4-dimethyl-3-isoxazolidinone;

[10] 2,4-D: (2,4-dichlorophenoxy)acetic acid, its esters and salts;

[11] diflufenican: N-(2,4-difluorophenyl)-2-[3-(trifluoromethyl)phenoxy]-3-pyridinecarboxamide;

[12] fentrazamide: N-cyclohexyl-N-ethyl-4-(2-chlorophenyl)-4,5-dihydro-5-oxo-1H-tetrazole-1-carboxamide;

[13] flufenacet: N-(4-fluorophenyl)-N-(1-methylethyl)-2-[[5-trifluoromethyl)-1,3,4-thiadiazol-2-yl]oxy]acetamide;

[14] imazethapyr: (±)-2-[4,5-dihydro-4-methyl-4-(1-methylethyl)-5-oxo-1H-imidazol-2-yl]-5-ethyl-3-pyridinecarboxylic acid;

[15] isoproturon: N,N-dimethyl-N'-[4-(1-methylethyl)phenyl]urea;

[16] linuron: N'(3,4-dichlorophenyl)-N-methoxy-N-methylurea;

[17] MCPA: (4-chloro-2-methylphenoxy)acetic acid, its esters and salts;

[18] MCPA-thioethyl: S-ethyl (4-chloro-2-methylphenoxy)ethanethioate;

[19] mefenacet: 2-(2-benzothiazolyloxy)-N-methyl-N-phenylacetamide;

[20] metributzin: 4-amino-6-(1,1-dimethylethyl)-3-(methylthio)-1,2,4-triazin-5(4H)-one;

[21] pendimethalin: N-(1-ethylpropyl)-3,4-dimethyl-2,6-dinitrobenzeneamine;

[22] penoxsulam: 2-(2,2-difluoroethoxy)-N-(5,8-dimethoxy-[1,2,4]triazole[1,5-c]pyrimidin-2-yl)-6-trifluoromethyl)benzenesulfonamide;

[23] picolinafen: N-(4-fluorophenyl)-6-[3-(trifluoromethyl)phenoxy]-2-pyridinecarboxamide;

[24] quinclorac: 3,7-dichloro-8-quinolinecarboxylic acid;
[25] thiobencarb: S-[(4-chlorophenyl)methyl]-diethylcarbamothioate;
[26] trifluralin: 2,6-dinitro-N,N-dipropyl-4-(trifluoromethyl)benzeneamine;
[27] ametryn: N-ethyl-N'-(1-methylethyl)-6-(methylthio)-1,3,5-triazine-2,4-diamine;
[28] asulam: methyl [(4-aminophenyl)-sulfonyl]-carbamate;
[29] atrazine: 6-chloro-N-ethyl-N'-(1-methylethyl)-1,3,5-triazine-2,4-diamine;
[30] bromoxynil: 3,5-dibromo-4-hydroxybenzonitrile, its potassium salt and its octanoic ester;
[31] clopyralid: 3,6-dichloro-2-pyridinecarboxylic acid;
[32] dicamba: 3,6-dichloro-2-methoxybenzoic acid and its salts;
[33] diuron: N'-(3,4-dichlorophenyl)-N,N-dimethyl-urea;
[34] fluoroxypyr: [(4-amino-3,5-dichloro-6-fluoro-2-pyridinyl)oxy]acetic acid and its esters;
[35] glufosinate-ammonium: ammonium (±)-2-amino-4-(hydroxymethylphosphinyl)butanoate;
[36] glyphosate: N-(phosphonomethyl)glycine and its salts;
[37] halosulfuron: 3-chloro-5-[[[[(4,6-dimethoxy-2-pyrimidinyl)amino]carboyl]amino]sulfonyl]-1-methyl-1H-pyrazole-4-carboxylic acid and its methyl ester;
[38] imazamox: 2-[4,5-dihydro-4-methyl-4-(1-methylethyl)-5-oxo-1H-imidazol-2-yl]-5-(methoxymethyl)-3-pyridinecarboxylic acid;
[39] imazapic: 2-[4,5-dihydro-4-methyl-4-(1-methylethyl)-5-oxo-1H-imidazol-2-yl]-5-methyl-3-pyridinecarboxylic acid, its salts and esters;
[40] ioxynil: 4-hydroxy-3,5-diiodobenzonitrile, its sodium salt and its octanoic ester;
[41] lactofen: (±)-2-ethoxy-1-ethyl-2-oxoethyl 5-[2-chloro-4-(trifluoromethyl)phenoxy]-2-nitrobenzoate;
[42] mesosulfuron: 2-[[[[(4,6-dimethoxy-2-pyrimidinyl)]amino]methyl]benzoic acid, its salts and esters;
[43] metolachlor: 2-chloro-N-(2-ethyl-6-methylphenyl)-N-(2-methoxy-1-methylethyl)acetamide;
[44] metsulfuron: 2-[[[[(4-methoxy-6-methyl-1,3,5-triazin-2-yl)amino]carbonyl]amino]sulfonyl]benzoic acid and its methyl ester;
[45] oxadiazon: 3-[2,4-dichloro-5-(1-methylethoxy)phenyl]-5-(1,1-dimethylethyl)-1,3,4-oxadiazol-2(3H)-one;
[46] paraquat: 1,1'-dimethyl-4,4'-bipyridinium;
[47] picloram: 4-amino-3,5,6-trichloro-2-pyridinecarboxylic acid and its potassium salt;
[48] pyraflufen-ethyl: ethyl 2-chloro-5-[4-chloro-5-(difluoromethoxy)-1-methyl-1H-pyrazol-3-yl]-4-fluorophenoxyacetate;
[49] sulfentrazone: N-[2,4-dichloro-5-[4-(difluoromethyl)-4,5-dihydro-3-methyl-5-oxo-1H-1,2,4-triazol-1-yl]phenyl]methanesulfonamide;
[50] triasulfuron: 2-(2-chloroethoxy)-N-[[4-methoxy-6-methyl-1,3,5-triazin-2-yl)amino]carbonyl]benzenesulfonamide;
[51] tribenuron: 2-[[[[(4-methoxy-6-methyl-1,3,5-triazin-2-yl)methylamino]carbonyl]sulfonyl]benzoic acid and its methyl ester;
[52] triclopyr: [(3,5,6-trichloro-2-pyridinyl)oxy]-acetic acid, its esters and salts;
[53] trifloxysulfuron: N-[[(4,6-dimethoxy-2-pyrimidinyl)amino]carbonyl]-3-(2,2,2-trifluoroethoxy)-2-pyridinesulfonamide;
[54] methylarsonic acid and its monosodium (MSMA) and disodium (DMSA) salts;
[55] prometryn: N,N'-bis(1-methylethyl)-6-(methylthio)-1,3,5-triazine-2,4-diamine;
[56] simazine: 6-chloro-N,N'-diethyl-1,3,5-triazine-2,4-diamine;
[57] mecoprop: 2-(4-chloro-2-methylphenoxy)propanoic acid, its salts and esters, in the presence of at least one inorganic or organic base.

Preferred components [B] in the above herbicidal compositions according to the present invention are: propanil, butachlor, pretilachlor, acetochlor, benfuresate, benzobicylcon, bromobutide, carfentrazone, clomazone, 2,4-D, diflufenican, fentrazamide, flufenacet, isoproturon, linuron, MCPA, mefenacet, metribuzin, pendimethalin, thiobencarb, picolinafen, trifluralin, ametryn, asulam, atrazine, bromoxynil, clopyralid, dicamba, diuron, fluroxipyr, glyphosate, imazapic, ioxynil, metholachlor, oxadiazon, paraquat, sulfentrazone, triclopyr, MSMA, DMSA, prometryn, mecoprop.

Preferred herbicidal compositions according to the present invention are those consisting of:
compound (I)+propanil;
compound (I)+propanil+base;
compound (I)+butachlor;
compound (I)+butachlor+base;
compound (I)+pretilachlor;
compound (I)+pretilachlor+base;
compound (I)+acetochlor;
compound (I)+acetochlor+base;
compound (I)+benfuresate;
compound (I)+benfuresate+base;
compound (I)+benzobicyclon;
compound (I)+benzobicylcon+base;
compound (I)+bromobutide;
compound (I)+bromobutide+base;
compound (I)+carfentrazone;
compound (I)+carfentrazone+base;
compound (I)+clomazone;
compound (I)+clomazone+base;
compound (I)+2,4-D;
compound (I)+2,4-D+base;
compound (I)+diflufenican;
compound (I)+diflufenican+base;
compound (I)+fentrazamide;
compound (I)+fentrazamide+base;
compound (I)+flufenacet;
compound (I)+flufenacet+base;
compound (I)+isoproturon;
compound (I)+isoproturon+base;
compound (I)+linuron;
compound (I)+linuron+base;
compound (I)+MCPA;
compound (I)+MCPA+base;
compound (I)+mefenacet;
compound (I)+mefenacet+base;
compound (I)+metribuzin;
compound (I)+metribuzin+base;
compound (I)+pendimethalin;
compound (I)+pendimethalin+base;
compound (I)+picolinafen;
compound (I)+picolinafen+base;
compound (I)+thiobencarb;
compound (I)+thiobencarb+base;
compound (I)+trifluralin;
compound (I)+trifluralin+base;
compound (I)+ametryn;
compound (I)+ametryn+base;
compound (I)+asulam;

compound (I)+asulam+base;
compound (I)+atrazine;
compound (I)+atrazine+base;
compound (I)+bromoxynil;
compound (I)+bromoxynil+base;
compound (I)+clopyralid;
compound (I)+clopyralid+base;
compound (I)+dicamba;
compound (I)+dicamba+base;
compound (I)+diuron;
compound (I)+diuron+base;
compound (I)+fluoroxipyr;
compound (I)+fluoroxipyr+base;
compound (I)+glyphosate;
compound (I)+glyphosate+base;
compound (I)+imazapic;
compound (I)+imazapic+base;
compound (I)+ioxynil;
compound (I)+ioxynil+base;
compound (I)+metolachlor;
compound (I)+metolachlor+base;
compound (I)+oxadiazon;
compound (I)+oxadiazon+base;
compound (I)+paraquat;
compound (I)+paraquat+base;
compound (I)+sulfentrazone;
compound (I)+sulfentrazone+base;
compound (I)+triclopyr;
compound (I)+triclopyr+base;
compound (I)+MSMA;
compound (I)+MSMA+base;
compound (I)+DMSA;
compound (I)+DMSA+base;
compound (I)+prometryn;
compound (I)+prometryn+base;
compound (I)+mecoprop;
compound (I)+mecoprop+base;
compound (I)+fentrazamide+bromobutide;
compound (I)+fentrazamide+bromobutide+base;
compound (I)+fentrazamide+benzobicyclon;
compound (I)+fentrazamide+benzobicyclon+base.

Preferred bases to be used in the above compositions are: sodium hydroxide, potassium hydroxide, calcium hydroxide, magnesium hydroxide, sodium carbonate, potassium carbonate, calcium carbonate, sodium bicarbonate, potassium bicarbonate, sodium hydride, calcium hydride, ammonia, methylamine, ethylamine, n-propylamine, isopropylamine, n-butylamine, sec-butylamine, tert-butylamine, n-pentylamine, isopentylamine, dimethylamine, N-ethylmethylamine, diethylamine, N-ethylpropylamine, diisopropylamine, trimethylamine, triethylamine, cyclohexylamine, pyrrolidine, N-methylpyrrolidine, morpholine, N-methylmorpholine, piperidine, N-methylpiperidine, pyridine, picoline, lutidine, 4-N,N-dimethylaminopyridine.

An object of the present invention also relates to the use of herbicidal compositions comprising a component [A] and a component [B], wherein component [A] is the compound having formula (I)

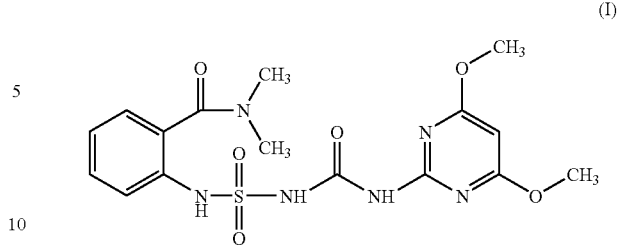

and component [B] consists of at least one product selected from the following herbicides:

[1] propanil: N-(3,4-dichlorophenyl)propanamide;
[2] butachlor: N-(butoxymethyl)-2-chloro-N-(2,6-diethylphenyl)acetamide;
[3] pretilachlor: 2-chloro-N-(2,6-diethylphenyl)-N-(2-propoxyethyl)acetamide;
[4] acetochlor: 2-chloro-N-(ethoxymethyl)-N-(2-ethyl-6-methylphenyl)acetamide;
[5] benfuresate: 2,3-dihydro-3,3-dimethyl-5-benzofuranylethanesulfonate;
[6] benzobicyclon: 3-[2-chloro-4-(methylsulfonyl)benzoyl]-4-(phenylthio)bicyclo[3.2.1]oct-3-en-2-one;
[7] bromobutide: 2-bromo-3,3-dimethyl-N-(1-methyl-1-phenylethyl)butaneamide;
[8] carfentrazone-ethyl: ethyl α,2-dichloro-5-[4-(difluoromethyl)-4,5-dihydro-3-methyl-5-oxo-1H,1,2,4-triazol-1-yl]-4-fluorobenzenepropanoate;
[9] clomazone: 2-[(chlorophenyl)methyl]-4,4-dimethyl-3-isoxazolidinone;
[10] 2,4-D: (2,4-dichlorophenoxy)acetic acid, its esters and salts;
[11] diflufenican: N-(2,4-difluorophenyl)-2-[3-(trifluoromethyl)phenoxy]-3-pyridinecarboxamide;
[12] fentrazamide: N-cyclohexyl-N-ethyl-4-(2-chlorophenyl)-4,5-dihydro-5-oxo-1H-tetrazole-1-carboxamide;
[13] flufenacet: N-(4-fluorophenyl)-N-(1-methylethyl)-2-[[5-trifluoromethyl)-1,3,4-thiadiazol-2-yl]oxy]acetamide;
[14] imazethapyr: (±)-2-[4,5-dihydro-4-methyl-4-(1-methylethyl)-5-oxo-1H-imidazol-2-yl]-5-ethyl-3-pyridinecarboxylic acid;
[15] isoproturon: N,N-dimethyl-N'-[4-(1-methylethyl)phenyl)urea;
[16] linuron: N'(3,4-dichlorophenyl)-N-methoxy-N-methylurea;
[17] MCPA: (4-chloro-2-methylphenoxy)acetic acid, its esters and salts;
[18] MCPA-thioethyl: S-ethyl (4-chloro-2-methylphenoxy) ethanethioate;
[19] mefenacet: 2-(2-benzothiazolyloxy)-N-methyl-N-phenylacetamide;
[20] metributzin: 4-amino-6-(1,1-dimethylethyl)-3-(methylthio)-1,2,4-triazin-5(4H)-one;
[21] pendimethalin: N-(1-ethylpropyl)-3,4-dimethyl-2,6-dinitrobenzeneamine;
[22] penoxsulam: 2-(2,2-difluoroethoxy)-N-(5,8-dimethoxy-[1,2,4]triazole[1,5-c]pyrimidin-2-yl)-6-trifluoromethyl)benzenesulfonamide;
[23] picolinafen: N-(4-fluorophenyl)-6-[3-(trifluoromethyl)phenoxy]-2-pyridinecarboxamide;
[24] quinclorac: 3,7-dichloro-8-quinolinecarboxylic acid;
[25] thiobencarb: S-[(4-chlorophenyl)methyl]-diethylcarbamothioate;
[26] trifluralin: 2,6-dinitro-N,N-dipropyl-4-(trifluoromethyl) benzeneamine;

[27] ametryn: N-ethyl-N'-(1-methylethyl)-6-(methylthio)-1,3,5-triazine-2,4-diamine;
[28] asulam: methyl [(4-aminophenyl)-sulfonyl]carbamate;
[29] atrazine: 6-chloro-N-ethyl-N'-(1-methylethyl)-1,3,5-triazine-2,4-diamine;
[30] bromoxynil: 3,5-dibromo-4-hydroxybenzonitrile, its potassium salt and its octanoic ester;
[31] clopyralid: 3,6-dichloro-2-pyridinecarboxylic acid;
[32] dicamba: 3,6-dichloro-2-methoxybenzoic acid and its salts;
[33] diuron: N'-(3,4-dichlorophenyl)-N,N-dimethyl-urea;
[34] fluoroxypyr: [(4-amino-3,5-dichloro-6-fluoro-2-pyridinyl)oxy]acetic acid and its esters;
[35] glufosinate-ammonium: ammonium (±)-2-amino-4-(hydroxymethylphosphinyl)butanoate;
[36] glyphosate: N-(phosphonomethyl)glycine and its salts;
[37] halosulfuron: 3-chloro-5-[[[[(4,6-dimethoxy-2-pyrimidinyl)amino]carboyl]amino]sulfonyl]-1-methyl-1H-pyrazole-4-carboxylic acid and its methyl ester;
[38] imazamox: 2-[4,5-dihydro-4-methyl-4-(1-methylethyl)-5-oxo-1H-imidazol-2-yl]-5-(methoxymethyl)-3-pyridinecarboxylic acid;
[39] imazapic: 2-[4,5-dihydro-4-methyl-4-(1-methylethyl)-5-oxo-1H-imidazol-2-yl]-5-methyl-3-pyridinecarboxylic acid, its salts and esters;
[40] ioxynil: 4-hydroxy-3,5-diiodobenzonitrile, its sodium salt and its octanoic ester;
[41] lactofen: (±)-2-ethoxy-1-ethyl-2-oxoethyl 5-[2-chloro-4-(trifluoromethyl)phenoxy]-2-nitrobenzoate;
[42] mesosulfuron: 2-[[[[(4,6-dimethoxy-2-pyrimidinyl)]amino]methyl]benzoic acid, its salts and esters;
[43] metolachlor: 2-chloro-N-(2-ethyl-6-methylphenyl)-N-(2-methoxy-1-methylethyl)acetamide;
[44] metsulfuron: 2-[[[[(4-methoxy-6-methyl-1,3,5-triazin-2-yl)amino]carbonyl]amino]sulfonyl]benzoic acid and its methyl ester;
[45] oxadiazon: 3-[2,4-dichloro-5-(1-methylethoxy)phenyl]-5-(1,1-dimethylethyl-1,3,4-oxadiazol-2(3H)-one;
[46] paraquat: 1,1'-dimethyl-4,4'-bipyridinium;
[47] picloram: 4-amino-3,5,6-trichloro-2-pyridinecarboxylic acid and its potassium salt;
[48] pyraflufen-ethyl: ethyl 2-chloro-5-[4-chloro-5-(difluoromethoxy)-1-methyl-1H-pyrazol-3-yl]-4-fluorophenoxyacetate;
[49] sulfentrazone: N-[2,4-dichloro-5-[4-(difluoromethyl)-4,5-dihydro-3-methyl-5-oxo-1H-1,2,4-triazol-1-yl]phenyl]methanesulfonamide;
[50] triasulfuron: 2-(2-chloroethoxy)-N-[[4-methoxy-6-methyl-1,3,5-triazin-2-yl)amino]carbonyl]benzenesulfonamide;
[51] tribenuron: 2-[[[[(4-methoxy-6-methyl-1,3,5-triazin-2-yl)methylamino]carbonyl]sulfonyl]benzoic acid and its methyl ester;
[52] triclopyr: [(3,5,6-trichloro-2-pyridinyl)oxy]-acetic acid, its esters and salts;
[53] trifloxysulfuron: N-[[(4,6-dimethoxy-2-pyrimidinyl)amino]carbonyl]-3-(2,2,2-trifluoroethoxy)-2-pyridinesulfonamide;
[54] methylarsonic acid and its monosodium (MSMA) and disodium (DMSA) salts;
[55] prometryn: N,N'-bis(1-methylethyl)-6-(methylthio)-1,3,5-triazine-2,4-diamine;
[56] simazine: 6-chloro-N,N'-diethyl-1,3,5-triazine-2,4-diamine;
[57] mecoprop: 2-(4-chloro-2-methylphenoxy)propanoic acid, its esters and salts;

optionally in the presence of at least one inorganic or organic base, for the control of weeds in agricultural crops.

Component [A] can be prepared according to what is described in patent application WO 98/40361.

Components [B] are known commercial products and are indicated herein with their common ISO name (International Standard Organization) and with the chemical names according to Chemical Abstracts. The structural formulae of these products, as also the main applications as herbicides are specified, among others, in "The Pesticide Manual" 13$^{th}$ edition (2003), Ed. C. D. S. Tomlin, published by the British Crop Protection Council, Farnham (UK).

As already mentioned, the use of the herbicidal compositions, object of the present invention, is advantageous with respect to the use of the single components [A] and [B], as, in addition to having a wider range of action, reduced doses of the products can be used for obtaining the same herbicidal effect; the compositions according to the present invention are effective in the post-emergence and pre-emergence control of numerous monocotyledon and dicotyledon weeds.

At the same time, said compositions have a reduced or zero phytotoxicity with respect to important agricultural crops thus making it possible to use them in the selective control of weeds.

Examples of weeds which can be effectively controlled using the compositions of the present invention are: *Abutilon theophrasti, Adonis* spp., *Ambrosia* spp., *Amaranthus* spp., *Amni maius, Anagallis arvensis, Anthemis* spp., *Aphanes arvensis, Atriplex patula, Bidens pilosa, Capsella bursa-pastoris, Chenopodium album, Convolvulus sepium, Datura stramonium, Euphorbia* spp., *Fumaria officinalis, Galeopsis tetrahit, Galinsoga ciliata, Galium aparine, Geranium* spp., *Helianthus* spp., *Ipomea* spp., *Kochia scoparia, Lamium* spp., *Lindernia procumbens, Matricaria* spp., *Monochoria vaginalis, Myosotis arvensis, Papaver rhoeas, Phaseolus aureus, Polygonum* spp., *Portulaca oleracea, Raphanus raphanistrum, Rotala indica, Rumex crispus, Senecio vulgaris, Sesbania exaltata, Sida spinosa, Sinapis arvensis, Solanum nigrum, Sonchus* spp., *Stellaria media, Thlaspi arvense, Veronica* spp., *Vicia* spp., *Viola* spp., *Xanthium* spp., *Aegilops tauschii, Alisma plantago, Alopecurus myosuroides, Apera* spp., *Avena fatua, Brachiaria* spp., *Bromus* spp., *Butomus umbellatus, Cenchrus echinatus, Commelina* spp., *Cynodon dactilon, Cyperus* spp., *Digitaria* spp., *Echinocloa* spp., *Elatina triandra, Eleocharis acicularis, Eleusine indica, Elymus repens, Eragrostis pilosa, Eriochloa villosa, Fimbristylis* spp., *Heteranthera* spp., *Leptochloa* spp., *Lolium* spp., *Panicum* spp., *Phalaris* spp., *Poa* spp., *Potamogeton nodosus, Sagittaria pygmaea, Scirpus* spp., *Setaria viridis, Sorghum* spp.

In particular, agrarian crops which can be advantageously treated with the compositions of the invention are: rice (*Oryza sativa*) for both sowing and transplanting, wheat (*Triticum* sp.), sugar cane (*Saccharum offininarum*), pastures, turf.

The compositions can also be used as total herbicides in burndown applications or in the weeding of industrial areas, railways, monuments, etc.

In the herbicidal compositions, object of the present invention, components [A] and [B] defined above can be mixed within a very wide ratio, in relation to various factors such as, for example: the component(s) [B] selected, the weeds to be attacked, the degree of infestation, the climatic conditions, the characteristics of the soil, the application method.

The ratio between the quantity by weight of component [A] and the quantity by weight of component(s) [B] can generally range from 1:0.01 to 1:10,000, preferably from 1:0.1 to 1:100.

When, for the purpose of stabilizing the compositions, at least one base is added to components [A] and [B], it/they can be used in extremely variable quantities, also in relation to the base(s) selected, and also the dosage and chemical structure of component(s) [B]; the quantity of base(s) can generally range from 0.1:1 to 200:1, preferably from 1:1 to 100:1 equivalents with respect to component [A].

For practical uses in agriculture, the herbicidal compositions, object of the present invention, can be applied in such quantities as to guarantee applicative doses of compound (I) ranging from 5-200 g/ha, preferably between 10-100 g/ha, and applicative doses of component(s) [B] ranging from 1-10,000 g/ha, preferably from 5-5,000 g/ha.

A further object of the present invention relates to a method for controlling weeds in agricultural crops by the application of the above compositions.

For practical uses in agriculture, it is appropriate to use the herbicidal compositions, object of the present invention, in the form of formulations which can be formulations already prepared or obtained at the moment of use. This can be achieved by either formulating component [A], component(s) [B] and the possible base(s) together, in the desired ratios, to give the final composition, or forming the composition at the moment of use by mixing the relative quantities of the possible base(s), component [A] and component(s) [B] formulated separately.

When the use of bases is envisaged, component [A], and/or possibly component(s) [B] if the chemical structure allows this, can be alternatively mixed to give the final composition in an already partially or totally salified form.

The herbicidal compositions according to the present invention therefore consist of formulations already prepared containing, in the desired ratios, component [A], component(s) [B] and the possible base(s) (ready-mix); or obtained at the moment of use by mixing the relative quantities of the possible base(s), component [A] and component(s) [B] formulated separately (tank-mix); or, when the use of bases is envisaged, obtained by mixing component [A], and/or possibly component(s) [B] in an already partially or totally salified form.

Compositions can be used in the form of dry powders, wettable powders, emulsifiable concentrates, microemulsions, pastes, granules, granules dispersible in water, solutions, suspensions, etc.: the choice of the type of composition will depend on the specific use.

Compositions in the form of wettable powders, granules, granules dispersible in water, are generally preferred.

The compositions are prepared according to known methods, for example by diluting or dissolving the active substance with a solvent medium and/or solid diluent, optionally adding surface-active agents, dispersing agents, stabilizers, etc. to the mixtures.

Inert solid diluents or supports which can be used are: kaolin, alumina, silica, talc, bentonite, gypsum, quartz, dolomite, attapulgite, montmorillonites, infusorial earth, cellulose, starch, etc.

Inert liquid diluents which can be used are water, or organic solvents such as aromatic hydrocarbons (xylols, alkylbenzol mixtures, etc.), aliphatic hydrocarbons (hexane, cyclohexane, etc.), halogenated aromatic hydrocarbons (chlorobenzol, etc.), alcohols (methanol, propanol, butanol, octanol, etc.), esters (isobutyl acetate, etc.), ketones (acetone, cyclohexanone, acetophenone, isophorone, ethylamylketone, etc.), or vegetable or mineral oils and mixtures thereof, etc.

Surface-active agents which can be used are wetting and emulsifying agents of the non-ionic type (polyethoxylated alkylphenols, polyethoxylated fatty alcohols, etc.), of the anionic type (alkylbenzenesulfonates, alkylsulfonates, etc.), of the cationic type (quaternary salts of alkylammonium, etc.).

Dispersing agents which can be used are for example lignin and its salts, cellulose derivatives, alginates, etc.

As already specified, whether compositions containing coformulated compounds are used, or compositions prepared at the moment of application by mixing components [A] and [B] already formulated, in many cases it may be convenient to stabilize the compositions by the addition of suitable quantities of inorganic or organic bases. Inorganic bases which can be used are, for example: hydrides or hydroxides of alkaline or alkaline-earth metals such as sodium hydride, calcium hydride, sodium hydroxyide, potassium hydroxide, calcium hydroxide, magnesium hydroxide; carbonates of alkaline metals such as sodium carbonate, potassium carbonate, calcium carbonate, sodium bicarbonate, potassium bicarbonate; ammonia; organic bases which can be used are, for example: primary, secondary or tertiary aliphatic amines, such as for example methylamine, ethylamine, n-propylamine, isopropylamine, n-butylamine, sec-butylamine, tert-butylamine, n-pentylamine, isopentylamine, dimethylamine, N-ethylmethylamine, diethylamine, N-ethylpropylamine, diisopropylamine, trimethylamine, triethylamine; cyclic aliphatic amines such as for example: cyclohexylamine, pyrrolidine, N-methylpyrrolidine, morpholine, N-methylmorpholine, piperidine, N-methylpiperidine; aromatic bases such as pyridine, picoline, lutidine, 4-N,N-dimethylaminopyridine, etc.

Other stabilizers can be added to the compositions, such as antioxidants, ultraviolet-ray absorbers, etc.

In order to widen the range of action of the above compositions, it is possible to add other active ingredients such as, for example, other herbicides, antidotes, fungicides, insecticides, acaricides, fertilizers, etc.

Examples of other herbicides which can be added to the compositions, object of the invention, are: acifluorfen, aclonifen, AKH-7088, amicarbazone, amitrole, anilofos, azafenidin, azimsulfuron, aziprotryne, BAY MKH 6561, benazolin, benfluralin, bensulfuron, bentazone, benzfendizone, benzofenap, benzthiazuron, bifenox, bilanafos, bispyribac-sodium, bromacil, bromofenoxim, butafenacil, butamifos, butenachlor, butralin, butroxydim, butylate, cafenstrole, carbetamide, chlomethoxyfen, chloramben, chlorbromuron, chlorbufam, chlorflurenol, chloridazon, chlorimuron, chlornitrofen, chloroxuron, chlorpropham, chlorthal, chlorthiamid, cinidon ethyl, cinmethylin, cinosulfuron, clethodim, clodinafop, clomeprop, cloransulam-methyl, cumyluron (JC-940), cyanazine, cycloate, cyclosulfamuron, cycloxydim, cyhalofop-butyl, 2,4-DB, daimuron, dalapon, desmedipham, desmetryn, dichlobenil, dichlorprop, dichlorprop-P, diclofop, diclosulam, diethatyl, difenoxuron, difenzoquat, diflufenzopyr, dimefuron, dimepiperate, dimethachlor, dimethametryn, dinitramine, dinoseb, dinoseb acetate, dinoterb, diphenamid, dipropetryn, diquat, dithiopyr, 1-eglinazine, endothal, EPTC, esprocarb, ethalfluralin, ethametsulfuronmethyl, ethidimuron, ethiozin (SMY 1500), ethofumesate, ethoxyfenethyl (HC-252), ethoxysulfuron, etobenzanid (HW 52), fenoxaprop, fenoxaprop-P, fenuron, flamprop, flamprop-M, flazasulfuron, florasulam, fluazifop, fluazifop-P, fluazolate (JV 485), flucarbazone-sodium, fluchloralin, flufenpyr ethyl, flumetsulam, flumicloracpentyl, flumioxazin, flumipropin, fluometuron, fluoroglycofen, fluoronitrofen, flupoxam, flupropanate, flupyrsulfuron, flurenol, fluridone, fluorochloridone, flurtamone, fluthiacet-methyl, fomesafen, foramsulfuron, fosamine, furyloxyfen, haloxyfop, haloxyfop-P-methyl, hexazinone, imazamethabenz, imazapyr, imazaquin, imazosulfuron, indanofan, iodosulfuron, isopropalin, isouron, isoxaben, isoxachlortole, isoxapyrifop, KPP-421, lenacil, LS830556, MCPB, metamitron, metazachlor, methabenzthiazuron, methazole, methoprotryne, methyldymron, metobenzuron, metobromuron, metosulam, metoxuron, molinate, monalide, monolinuron, naproanilide, napropamide, naptalam, NC-330, neburon, nicosulfuron, nipyraclofen, norflurazon, orbencarb, oryzalin, oxadiargyl, oxasulfuron, oxaziclomefone, oxyfluorfen, pebulate, pentanochlor, pentoxazone, phenmedipham, piperophos, primisulfuron, prodiamine, profluazol, proglinazine, prometon, propaquizafop, propazine, propham, propisochlor, propyzamide, prosulfocarb, prosulfuron, pyraclonil, pyrazogyl (HSA-961), pyrazolynate, pyrazoxyfen, pyribenzoxim, pyributicarb, pyridafol, pyridate, pyriftalid, pyriminobac-methyl, pyrithiobac-sodium, quinmerac, quizalofop, quizalofop-P, rimsulfuron, sethoxydim, siduron, simetryn, sulfometuron-methyl, 2,3,6-TBA, TCA-sodium, tebutam, tebuthiuron, tepraloxydim, terbacil, terbumeton, terbutryn, thenylchlor, thiazafluoron, thiazopyr, thidiazimin, thiobencarb, tiocarbazil, tioclorim, tralkoxydim, triallate, triaziflam, trietazine, triflusulfuron-methyl, tritosulfuron, UBI-C4874, vernolate.

Examples of antidotes which can be added to the compositions to improve their phytotoxicity with respect to agricultural crops are: cloquintocet-mexyl, dimepiperate, dymron, fenchlorazole-ethyl, fenclorim, furilazole, isoxadifen-ethyl, mefenpyr-diethyl.

The concentration of active substances [A]+[B], in the above compositions can vary within a wide range, depending on the active principles selected, the applications for which they are destined and the type of formulation. The overall composition of active substances can generally range from 1 to 90%, preferably from 5 to 75%.

The following examples are provided for a better illustration of the invention.

EXAMPLE 1 a) Determination of the Herbicidal Activity and Phytotoxicity in Post-Emergence

The herbicidal activity in post-emergence of the compositions of the invention was evaluated according to the following operating procedures.

The vegetable species of interest (weeds or crops) were planted in vases having an upper diameter of 10 cm, a height of 10 cm and containing sandy earth.

Water was added to each vase in a suitable quantity for the germination of the seeds. Fifteen days after planting (ten in the case of wheat), i.e. when the weed seedlings and crops, depending on the species, had reached a height of 10-15 cm, the vases were divided into three groups and treated respectively with: a) an aqueous dispersion of component [A] at a dosage $D_A$; b) an aqueous dispersion of component [B] at a dosage $D_B$; c) an aqueous dispersion containing components [A] and [B] at dosages, $D_A$ e $D_B$, respectively.

All the vases were kept under observation in a conditioned environment under the following environmental conditions:
temperature: 24° C.;
relative humidity: 60%;
photo-period: 16 ore;
light intensity: 10,000 lux.
Every two days the vases were uniformly watered to ensure a sufficient humidity degree for a good growth of the plants.

Twenty-one days after treatment, the herbicidal activity was evaluated (expressed as a % of the damage observed on the vegetable species) for the composition ($E_C$) and for the two components [A] and [B] tested separately ($E_A$, $E_B$).

b) Determination of the Herbicidal Activity and Phytotoxicity in Pre-Emergence

The herbicidal activity in pre-emergence of the compounds of the invention was evaluated according to the following operating procedures.

The vegetable species of interest (weeds or crops) were planted in vases having an upper diameter of 10 cm, a height of 10 cm and containing sandy earth.

Water was added to each vase in a suitable quantity for the germination of the seeds. One day after planting, the vases were divided into three groups and treated respectively with a) an aqueous dispersion of component [A] at a dosage $D_A$; b) an aqueous dispersion of component [B] at a dosage $D_B$; c) an aqueous dispersion containing components [A] and [B] at dosages $D_A$ and $D_B$, respectively.

All the vases were kept under observation in a conditioned environment under the following environmental conditions:
temperature: 24° C.;
relative humidity: 60%;
photo-period: 16 ore;
light intensity: 10,000 lux.
Every two days the vases were uniformly watered to ensure a sufficient humidity degree for a good growth of the plants.

Four weeks after treatment, the herbicidal activity was evaluated (expressed as a % of the damage observed on the vegetable species) for the composition ($E_C$) and for the components [A] and [B] tested separately ($E_A$, $E_B$).

A synergistic effect was observed when the determined experimental herbicidal activity of the composition, $E_C$, proved to be higher than that calculated applying the Colby formula ("Weeds", 15 (1967), pages 20-22):

$$E_{teor} = E_A + E_B - E_A \times E_B / 100$$

wherein:
$E_{teor}$=activity calculated for the composition consisting of [A] at a dosage $D_A$+[B] at a dosage $D_B$;
$E_A$=activity observed for [A] at a dosage $D_A$;
$E_B$=activity observed for [B] at a dosage $D_B$.

Tested weeds were *Abutilon theophrasti, Ambrosia artemisiifolia, Amaranthus retroflexus, Amni maius, Capsella bursa-pastoris, Chenopodium album, Convolvulus sepium, Galium aparine, Ipomea purpurea, Matricaria camomilla, Monochoria vaginalis, Papaver rhoeas, Phaseolus aureus, Portulaca oleracea, Raphanus raphanistrum, Rotala indica, Senecio vulgaris, Sida spinosa, Sinapis arvensis, Solanum nigrum, Stellaria media, Veronica persica, Viola arvensis, Alisma plantago, Alopecurus myosuroides, Apera spica ventis, Avena fatua, Commelina benghalensis, Cyperus difformis, Digitaria sanguinalis, Echinocloa crusgalli, Eleocharis acicularis, Eleusine indica, Heteranthera sp., Lolium multiflorum, Panicum maximum, Poa annua, Sagittaria pygmaea, Scirpus juncoides, Setaria viridis, Sorghum alepensis.*

The applied doses of component [A] ranged between 15-60 g/ha (post-emergence) and 30-100 g/ha (pre-emergence). The doses of components [B] varied widely depending on the compound and the type of application.

Here below are reported the components [B] which gave, in admixture with component [A], an herbicidal activity of 85-100% against a number of economically important weeds, compared with an expected activity of 40-70% according to Colby formula; the possibility of using the compositions with compound (I) in selective or non-selective treatments, are reported in brackets:

propanil (rice), butachlor (rice), pretilachlor (rice), acetochlor (rice), benfuresate (rice), benzobicyclon (rice), bromobutide (rice), carfentrazone (rice, cereals, sugarcane, burndown), chlorotoluron (cereals), clomazone (rice, sugarcane), 2,4-D (cereals, pastures, turf, burndown), diflufenican (cereals), fentrazamide (rice), flufenacet (cereals), imazethapyr (rice), isoproturon (cereals), linuron (cereals), MCPA (rice, cereals, turf), mefenacet (rice), metribuzin (cereals, sugarcane, turf, burndown, lay-by), pendimethalin (rice, cereals, turf, burndown), penoxsulam (rice), picolinafen (cereals), quinclorac (rice), thiobencarb (rice), trifluralin (cereals), ametryn (sugarcane), asulam (sugarcane, turf, lay-by), atrazine (sugarcane, turf), bromoxynil (cereals, turf), clopyralid (cereals, pastures, turf), dicamba (cereals, pastures, turf, burndown), diuron (sugarcane, burndown, lay-by), fluoroxypyr (cereals, pastures), glufosinate (burndown, lay-by), glyphosate (sugarcane, burndown, lay-by), halosulfuron (rice, sugarcane), imazamox (rice), imazapic (sugarcane), ioxynil (cereals, turf), lactofen (burndown, lay-by), mesosulfuron (cereals), metolachlor (burndown, lay-by), metsulfuron (rice, turf), oxadiazon (rice, turf), paraquat (burndown, lay-by), picloram (pastures), pyraflufen (cereals, sugarcane, burndown), sulfentrazone (cereals, sugarcane, turf), triasulfuron (cereals), tribenuron (cereals), triclopyr (turf, pastures), trifloxisulfuron (sugarcane), MSMA (turf, burndown, lay-by), DMSA (turf, burndown), prometryn (burndown, lay-by), simazine (turf), mecoprop (cereals).

EXAMPLE 2

Preparation of Ready-Mix Compositions of Compound (I)+Propanil as Granules Dispersible in Water Composition C1a.
A mixture in powder form containing the following products is prepared by grinding in a mill of the Jet Mill type:

| | |
|---|---|
| technical compound (I) at 98%: | 8.0 g (18.5 mmoles) |
| technical propanil at 96%, comp. [B]: | 187.5 g |
| sodium ligninsulfonate: | 36.0 g |
| sodium alkylnaphthalenesulfonate: | 6.0 g |
| silica: | 12.0 g |
| kaolin: | 50.0 g |

The mixture in powder form is then humidified with water and sent to an extruder of the Dome type. The wet granules thus obtained are then dried in a fluid bed dryer and sieved to give the composition C1a.

Composition C1b.
A mixture in powder form containing the following products is prepared by grinding in a mill of the Jet Mill type:

| | |
|---|---|
| technical compound (I) at 98%: | 8.0 g (18.5 mmoles) |
| technical propanil at 96%, comp. [B]: | 187.5 g |
| sodium ligninsulfonate: | 36.0 g |
| sodium alkylnaphthalenesulfonate: | 6.0 g |
| silica: | 12.0 g |
| kaolin: | 50.0 g |

The mixture in powder form is then humidified with water containing 1.2 g (30 mmoles) of sodium hydroxide and sent to an extruder of the Dome type. The wet granules thus obtained are then dried in a fluid bed dryer and sieved to give the composition C1b.

EXAMPLE 3

Preparation of Ready-Mix Compositions of Compound (I)+Butachlor as Granules

Composition C2a.
A powder is prepared by adsorption on silica of the following components:

| | |
|---|---|
| technical butachlor at 96%, comp. [B]: | 12.0 g |
| polyethoxylated styrylphenol: | 3.0 g |
| silica: | 15.0 g |

The powder thus obtained is mixed thoroughly until a homogeneous mixture is obtained, with:

| | |
|---|---|
| compound (I) at 98%, comp. [A]: | 1.0 g (2.3 mmoles) |
| sodium ligninsulfonate: | 3.0 g |
| kaolin: | 265.0 g |

The mixture thus obtained is humidified with water and sent to an extruder of the Dome type. The wet granules obtained are then dried in a fluid bed dryer and sieved to give the composition C2a.

Composition C2b.
A powder is prepared by adsorption on silica of the following components:

| | |
|---|---|
| technical butachlor at 96%, comp. [B]: | 12.0 g |
| polyethoxylated styrylphenol: | 3.0 g |
| silica: | 15.0 g |

The powder thus obtained is mixed thoroughly until a homogeneous mixture is obtained, with:

| | |
|---|---|
| compound (I) at 98%, comp. [A]: | 1.0 g (2.3 mmoles) |
| sodium ligninsulfonate: | 3.0 g |
| sodium carbonate: | 1.5 g (14.15 mmoles) |
| kaolin: | 265.0 g |

The mixture thus obtained is humidified with water and sent to an extruder of the Dome type. The wet granules obtained are then dried in a fluid bed dryer and sieved to give the composition C2b.

EXAMPLE 4

Storage Stability of Compositions C1a, C1b, C2a, C2b

Aliquots of compositions C1a, C1b, C2a and C2b, prepared as described in Example 3, were stored in oven at 54° C. for 14 days.

After cooling at room temperature, the samples were analyzed by HPLC-UV-DAD for the active ingredients content determination.

The results were compared with those obtained analyzing aliquots of compositions C1a, C1b, C2a and C2b stored for 14 days at room temperature:

|  | % (I) | (% loss) |  | (% loss) |
|---|---|---|---|---|
|  |  |  | % propanil |  |
| C1a (14 d at 22° C.) | 2.62 | — | 59.9 | — |
| C1a (14 d at 54° C.) | 1.83 | (43.2) | 59.8 | (0.2) |
| C1b (14 d at 22° C.) | 2.63 | — | 60.3 | — |
| C1b (14 d at 54° C.) | 2.62 | (0.4) | 60.1 | (0.3) |
|  |  |  | % butachlor |  |
| C2a (14 d at 22° C.) | 0.34 | — | 3.85 | — |
| C2a (14 d at 54° C.) | 0.22 | (54.5) | 3.84 | (0.3) |
| C2b (14 d at 22° C.) | 0.35 | — | 3.86 | — |
| C2b (14 d at 54° C.) | 0.35 | (0.0) | 3.84 | (0.5) |

From these data it is evident that the addition of a base greatly increases the stability at the storage of compound (I), allowing a more reliable utilization of the ready-mix compositions for field applications.

EXAMPLE 5

By operating with methods analogous to those described above, the compositions indicated in the following table were prepared:

TABLE

| Composition | [A] + [B] + base |
|---|---|
| C1a | compound (I) + propanil |
| C1b | compound (I) + propanil + NaOH |
| C2a | compound (I) + butachlor |
| C2b | compound (I) + butachlor + $Na_2CO_3$ |
| C3a | compound (I) + pretilachlor |
| C3b | compound (I) + pretilachlor + NaOH |
| C4a | compound (I) + acetochlor; |
| C4b | compound (I) + acetochlor + $Na_2CO_3$ |
| C5a | compound (I) + benfuresate |
| C5b | compound (I) + benfuresate + NaOH |
| C6a | compound (I) + benzobicyclon |
| C6b | compound (I) + benzobicyclon + $Na_2CO_3$ |
| C7a | compound (I) + bromobutide |
| C7b | compound (I) + bromobutide + $Mg(OH)_2$ |
| C8a | compound (I) + chlorotoluron |
| C8b | compound (I) + chlorotoluron + NaOH |
| C9a | compound (I) + clomazone |
| C9b | compound (I) + clomazone + $Na_2CO_3$ |
| C10a | compound (I) + 2,4-D |
| C10b | compound (I) + 2,4-D + NaOH |
| C11a | compound (I) + diflufenican |
| C11b | compound (I) + diflufenican + $Na_2CO_3$ |
| C12a | compound (I) + fentrazamide |
| C12b | compound (I) + fentrazamide + $Na_2CO_3$ |
| C13a | compound (I) + flufenacet |
| C13b | compound (I) + flufenacet + KOH |
| C14a | compound (I) + imazethapyr |
| C14b | compound (I) + imazethapyr + $NH_3$ |
| C15a | compound (I) + isoproturon |
| C15b | compound (I) + isoproturon + $Na_2CO_3$ |
| C16a | compound (I) + linuron |
| C16b | compound (I) + linuron + $K_2CO_3$ |
| C17a | compound (I) + MCPA |
| C17b | compound (I) + MCPA + $Na_2CO_3$ |
| C18a | compound (I) + MCPA-thioethyl |
| C18b | compound (I) + MCPA-thioethyl + $Na_2CO_3$ |
| C19a | compound (I) + mefenacet |
| C19b | compound (I) + mefenacet + $Na_2CO_3$ |
| C20a | compound (I) + metribuzin |
| C20b | compound (I) + metribuzin + $Na_2CO_3$ |
| C21a | compound (I) + pendimethalin |

TABLE-continued

| Composition | [A] + [B] + base |
|---|---|
| C21b | compound (I) + pendimethalin + NAOH |
| C22a | compound (I) + penoxsulam |
| C22b | compound (I) + penoxsulam + trietilammina |
| C23a | compound (I) + picolinafen |
| C23b | compound (I) + picolinafen + $Na_2CO_3$ |
| C24a | compound (I) + quinclorac |
| C24b | compound (I) + quinclorac + triethylamine |
| C25a | compound (I) + thiobencarb |
| C25b | compound (I) + thiobencarb + $Na_2CO_3$ |
| C26a | compound (I) + trifluralin |
| C26b | compound (I) + trifluralin + NaOH |
| C27a | compound (I) + ametryn |
| C27b | compound (I) + ametryn + $Na_2CO_3$ |
| C28a | compound (I) + asulam |
| C28b | compound (I) + asulam + $Na_2CO_3$ |
| C29a | compound (I) + atrazine |
| C29b | compound (I) + atrazine + $Na_2CO_3$ |
| C30a | compound (I) + bromoxynil |
| C30b | compound (I) + bromoxynil + KHO |
| C31a | compound (I) + clopyralid |
| C31b | compound (I) + clopyralid + NaOH |
| C32a | compound (I) + dicamba |
| C32b | compound (I) + dicamba + NaOH |
| C33a | compound (I) + diuron |
| C33b | compound (I) + diuron + $Na_2CO_3$ |
| C34a | compound (I) + fluroxypyr |
| C34b | compound (I) + fluroxypyr + $NaHCO_3$ |
| C35a | compound (I) + glufosinate-ammonium |
| C35b | compound (I) + glufosinate-ammonium + $NH_3$ |
| C36a | compound (I) + glyphosate |
| C36b | compound (I) + glyphosate + isopropylamine |
| C37a | compound (I) + halosulfuron |
| C37b | compound (I) + halosulfuron + $NaHCO_3$ + NaOH |
| C38a | compound (I) + imazamox |
| C38b | compound (I) + imazamox + $NaHCO_3$ + NaOH |
| C39a | compound (I) + imazapic |
| C39b | compound (I) + imazapic + $NaHCO_3$ + NaOH |
| C40a | compound (I) + ioxynil |
| C40b | compound (I) + ioxynil + NaOH |
| C41a | compound (I) + lactofen |
| C41b | compound (I) + lactofen + $NaHCO_3$ |
| C42a | compound (I) + mesosulfuron |
| C42b | compound (I) + mesosulfuron + $NaHCO_3$ + NaOH |
| C43a | compound (I) + metolachlor |
| C43b | compound (I) + metolachlor + $Na_2CO_3$ |
| C44a | compound (I) + metsulfuron |
| C44b | compound (I) + metsulfuron + $NaHCO_3$ + NaOH |
| C45a | compound (I) + oxadiazon |
| C45b | compound (I) + oxadiazon + $Na_2CO_3$ |
| C46a | compound (I) + paraquat |
| C46b | compound (I) + paraquat + $NaHCO_3$ |
| C47a | compound (I) + picloram |
| C47b | compound (I) + picloram + KOH |
| C48a | compound (I) + pyraflufen-ethyl |
| C48b | compound (I) + pyraflufen-ethyl + $NaHCO_3$ |
| C49a | compound (I) + sulfentrazone |
| C49b | compound (I) + sulfentrazone + $NaHCO_3$ |
| C50 | compound (I) + triasulfuron |
| C50 | compound (I) + triasulfuron + $Na_2CO_3$ |
| C51a | compound (I) + tribenuron |
| C51b | compound (I) + tribenuron + KOH |
| C52a | compound (I) + triclopyr |
| C52b | compound (I) + triclopyr + triethylamine |
| C53a | compound (I) + trifloxisulfuron |
| C53b | compound (I) + trifloxisulfuron + $Na_2CO_3$ |
| C54a | compound (I) + MSMA |
| C54b | compound (I) + MSMA + $NaHCO_3$ |
| C54c | compound (I) + DMSA |
| C54d | compound (I) + DMSA + NaOH |
| C55a | compound (I) + prometryn |
| C55b | compound (I) + prometryn + $NaHCO_3$ |
| C56a | compound (I) + simazine |
| C56b | compound (I) + simazine + $NaHCO_3$ |
| C57a | compound (I) + mecoprop |
| C57b | compound (I) + mecoprop + $Na_2CO_3$ |
| C58a | compound (I) + fentrazamide + bromobutide |

TABLE-continued

| Composition | [A] + [B] + base |
|---|---|
| C58b | compound (I) + fentrazamide + bromobutide + Mg(OH)$_2$ |
| C59a | compound (I) + fentrazamide + benzobi-cyclon |
| C59b | compound (I) + fentrazamide + benzobi-cyclon + Na$_2$CO$_3$ |

The invention claimed is:

1. A herbicidal composition comprising a component [A] and a component [B], where component [A] is the compound having formula (I)

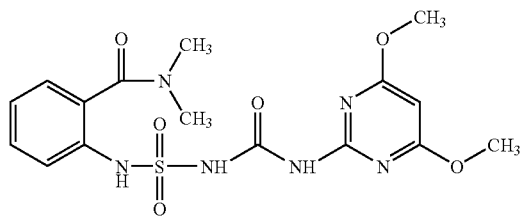

and component [B] comprises at least one known herbicide selected from the group consisting of:
propanil: N-(3,4-dichlorophenyl)propanamide;
pretilachlor: 2-chloro-N-(2,6-diethylphenyl)-N-(2-propoxyethyl)acetamide;
acetochlor: 2-choro-N-(ethoxymethyl)-N-(2-ethyl-6-methylphenyl)acetamide;
benzobicyclon: 3-[2-chloro-4-(methylsulfonyl)-benzoyl]-4-(phenylthio)bicyclo[3.2.1]oct-3-en-2-one;
bromobutide: 2-bromo-3,3-dimethyl-N-(1-methyl-1-phenylethyl)butaneamide;
carfentrazone-ethyl: ethyl α,2-dichloro-5-[4-(difluoromethyl)-4,5-dihydro-3-methyl-5-oxo-1H, 1,2,4-triazol-1-yl]-4-fluorobenzenepropanoate;
clomazone: 2-[(chlorophenyl)methyl]-4,4-dimethyl-3-isoxazolidinone;
2,4-D: (2,4-dichlorophenoxy)acetic acid, its esters and salts;
fentrazamide: N-cyclohexyl-N-ethyl-4-(2-chlorophenyl)-4,5-dihydro-5-oxo-1H-tetrazole-1-carboxamide;
imazethapyr: (±)-2-[4,5-dihydro-4-methyl-4-(1-methylethyl)-5-oxo-1H-imidazol-2-yl]-5-ethyl-3-pyridinecarboxylic acid;
pendimethalin: N-(1-ethylpropyl)-3,4-dimethyl-2,6-dinitrobenzeneamine;
quinclorac: 3,7-dichloro-8-quinolinecarboxylic acid;
atrazine: 6-chloro-N-ethyl-N'-(1-methylethyl)-1,3,5-triazine-2,4-diamine;
dicamba: 3,6-dichloro-2-methoxybenzoic acid and its salts;
glufosinate-ammonium: ammonium (±)-2-amino-4-(hydroxymethylphosphinyl)butanoate;
glyphosate: N-(phosphonomethyl)glycine and its salts;
halosulfuron: 3-chloro-5-[[[[(4,6-dimethoxy-2-pyrimidinyl)amino]carboyl]amino]sulfonyl]-1-methyl-1H-pyrazole-4-carboxylic acid and its methyl ester;
imazamox: 2-[4,5-dihydro-4-methyl-4-(1-methylethyl)-5-oxo-1H-imidazol-2-yl]-5-(methoxymethyl)-3-pyridine-carboxylic acid;
imazapic: 2-[4,5-dihydro-4-methyl-4-(1-methylethyl)-5-oxo-1H-imidazol-2-yl]-5-methyl-3-pyridinecarboxylic acid, its salts and esters;
metolachlor: 2-chloro-N-(2-ethyl-6-methyl-phenyl)-N-(2-methoxy-1-methylethyl)acetamide;
metsulfuron: 2-[[[[(4-methoxy-6-methyl-1,3,5-triazin-2-yl)amino]carbonyl]amino]sulfonyl]benzoic acid and its methyl ester;
oxadiazon: 3-[2,4-dichloro-5-(1-methylethoxy)-phenyl]-5-(1,1-dimethylethyl-1,3,4-oxadiazol-2(3H)-one;
picloram: 4-amino-3,5,6-trichloro-2-pyridine-carboxylic acid and its potassium salt;
sulfentrazone: N-[2,4-dichloro-5-[4-(difluoromethyl)-4,5-dihydro-3-methyl-5-oxo-1H-1,2,4-triazol-1-yl]phenyl]methanesulfonamide;
triclopyr: [(3,5,6-trichloro-2-pyridinyl)oxy]-acetic acid, its esters and salts;
trifloxysulfuron: N-[[(4,6-dimethoxy-2-pyrimidinyl)amino]carbonyl]-3-(2,2,2-trifluoroethoxy)-2-pyridinesulfonamide;
simazine: 6-chloro-N,N'-diethyl-1,3,5-triazine-2,4-diamine;
optionally in the presence of at least one inorganic or organic base.

2. The herbicidal composition according to claim 1, wherein the ratio between the quantity by weight of component [A] and the quantity by weight of component(s) [B] ranges from 1:0.01 to 1:10,000.

3. The herbicidal composition according to claim 1, wherein the applicative quantities of compound (I) are within the range of 5-200 g/ha.

4. The herbicidal composition according to claim 1, wherein the applicative doses of component(s) [B] are within the range of 1-10,000 g/ha.

5. The herbicidal composition according to claim 1, which is in the form of a dry powder, a wettable powder, an emulsifying concentrate, a micro-emulsion, a paste, a granule, a granule dispersible in water, a solution and a suspension.

6. The herbicidal composition according to claim 1, which is in the form of a wettable powder, a granule, and a granule dispersible in water.

7. The herbicidal composition according to claim 1, which is in the form of a already prepared formulation comprising component [A] and component(s) [B] and optionally the at least one inorganic or organic base; or which is prepared for use by mixing component [A] and component(s) [B], formulated separately and optionally with the at least one inorganic or organic base; or, mixing component [A], component(s) [B] or both [A] and [B] in which are in a partially or totally salified form.

8. The herbicidal composition according to claim 1, further comprising at least one additional ingredient selected from the group consisting of a herbicide, an antidote, a fungicide, an insecticide, an acaricide, and a fertilizer.

9. The herbicidal composition according to claim 8, wherein the concentration of active substances, also comprising [A]+[B], is from 1 to 90%.

10. The herbicidal composition according to claim 9, wherein the concentration is from 5 to 75%.

11. A method for the control of weeds in agricultural crops comprising applying to said crops a herbicidal composition comprising a component [A] and a component [B], wherein component [A] is the compound having formula (I)

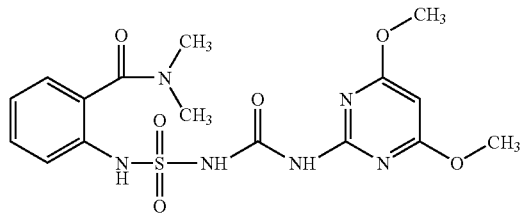

and component [B] comprises at least one herbicide selected from the group consisting of:
propanil: N-(3,4-dichlorophenyl)propanamide;
pretilachlor: 2-chloro-N-(2,6-diethylphenyl)-N-(2-propoxyethyl)acetamide;
acetochlor: 2-choro-N-(ethoxymethyl)-N-(2-ethyl-6-methylphenyl)acetamide;
benzobicyclon: 3-[2-chloro-4-(methyl-sulfonyl)-benzoyl]-4-(phenylthio)bicyclo[3.2.1]oct-3-en-2-one;
bromobutide: 2-bromo-3,3-dimethyl-N-(1-methyl-1-phenylethyl)butaneamide;
carfentrazone-ethyl: ethyl α,2-dichloro-5-[4-(difluoromethyl)-4,5-dihydro-3-methyl-5-oxo-1H, 1,2,4-triazol-1-yl]-4-fluorobenzenepropanoate;
clomazone: 2-[(chlorophenyl)methyl]-4,4-dimethyl-3-isoxazolidinone;
2,4-D: (2,4-dichlorophenoxy)acetic acid, its esters and salts;
fentrazamide: N-cyclohexyl-N-ethyl-4-(2-chlorophenyl)-4,5-dihydro-5-oxo-1H-tetrazole-1-carboxamide;
imazethapyr: (±)-2-[4,5-dihydro-4-methyl-4-(1-methylethyl)-5-oxo-1H-imidazol-2-yl]-5-ethyl-3-pyridinecarboxylic acid;
pendimethalin: N-(1-ethylpropyl)-3,4-dimethyl-2,6-dinitrobenzeneamine;
quinclorac: 3,7-dichloro-8-quinolinecarboxylic acid;
atrazine: 6-chloro-N-ethyl-N'-(1-methylethyl)-1,3,5-triazine-2,4-diamine;
dicamba: 3,6-dichloro-2-methoxybenzoic acid and its salts;
glufosinate-ammonium: ammonium (±)-2-amino-4-(hydroxymethylphosphinyl)butanoate;
glyphosate: N-(phosphonomethyl)glycine and its salts;
halosulfuron: 3-chloro-5-[[[[(4,6-dimethoxy-2-pyrimidinyl)amino]carboyl]amino]sulfonyl]-1-methyl-1H-pyrazole-4-carboxylic acid and its methyl ester;
imazamox: 2-[4,5-dihydro-4-methyl-4-(1-methylethyl)-5-oxo-1H-imidazol-2-yl]-5-(methoxymethyl)-3-pyridinecarboxylic acid;
imazapic: 2-[4,5-dihydro-4-methyl-4-(1-methylethyl)-5-oxo-1H-imidazol-2-yl]-5-methyl-3-pyridinecarboxylic acid, its salts and esters;
metolachlor: 2-chloro-N-(2-ethyl-6-methyl-phenyl)-N-(2-methoxy-1-methylethyl)acetamide;
metsulfuron: 2-[[[[(4-methoxy-6-methyl-1,3,5-triazin-2-yl)amino]carbonyl]amino]sulfonyl]benzoic acid and its methyl ester;
oxadiazon: 3-[2,4-dichloro-5-(1-methylethoxy)-phenyl]-5-(1,1-dimethylethyl-1,3,4-oxadiazol-2(3H)-one;
picloram: 4-amino-3,5,6-trichloro-2-pyridine-carboxylic acid and its potassium salt;
sulfentrazone: N-[2,4-dichloro-5-[4-(difluoromethyl)-4,5-dihydro-3-methyl-5-oxo-1H-1,2,4-triazol-1-yl]phenyl]methanesulfonamide;
triclopyr: [(3,5,6-trichloro-2-pyridinyl)oxy]-acetic acid, its esters and salts;
trifloxysulfuron: N-[[(4,6-dimethoxy-2-pyrimidinyl)amino]carbonyl]-3-(2,2,2-trifluoroethoxy)-2-pyridinesulfonamide;
simazine: 6-chloro-N,N'-diethyl-1,3,5-triazine-2,4-diamine;
optionally in the presence of at least one inorganic or organic base.

12. A method for post-emergence and pre-emergence control of a monocotyledon and dicotyledon weed, for the treatment of an agricultural crop, a meadow, a lawn, and/or as a herbicide in pre-sowing applications, or weeding of an industrial area, a railway, and a monument, wherein the method comprises applying to said weed, agricultural crop, meadow, lawn, industrial area, railway or monument, a herbicidal composition comprising a component [A] and a component [B], wherein component [A] is the compound having formula (I)

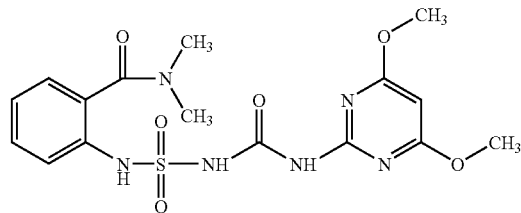

and component [B] comprises at least one herbicide selected from the group consisting of:
propanil: N-(3,4-dichlorophenyl)propanamide;
pretilachlor: 2-chloro-N-(2,6-diethylphenyl)-N-(2-propoxyethyl)acetamide;
acetochlor: 2-choro-N-(ethoxymethyl)-N-(2-ethyl-6-methylphenyl)acetamide;
benzobicyclon: 3-[2-chloro-4-(methyl-sulfonyl)-benzoyl]-4-(phenylthio)bicyclo[3.2.1]oct-3-en-2-one;
bromobutide: 2-bromo-3,3-dimethyl-N-(1-methyl-1-phenylethyl)butaneamide;
carfentrazone-ethyl: ethyl α,2-dichloro-5-[4-(difluoromethyl)-4,5-dihydro-3-methyl-5-oxo-1H,1,2,4-triazol-1-yl]-4-fluorobenzenepropanoate;
clomazone: 2-[(chlorophenyl)methyl]-4,4-dimethyl-3-isoxazolidinone;
2,4-D: (2,4-dichlorophenoxy)acetic acid, its esters and salts;
fentrazamide: N-cyclohexyl-N-ethyl-4-(2-chlorophenyl)-4,5-dihydro-5-oxo-1H-tetrazole-1-carboxamide;
imazethapyr: (±)-2-[4,5-dihydro-4-methyl-4-(1-methylethyl)-5-oxo-1H-imidazol-2-yl]-5-ethyl-3-pyridinecarboxylic acid;
pendimethalin: N-(1-ethylpropyl)-3,4-dimethyl-2,6-dinitrobenzeneamine;
quinclorac: 3,7-dichloro-8-quinolinecarboxylic acid;
atrazine: 6-chloro-N-ethyl-N'-(1-methylethyl)-1,3,5-triazine-2,4-diamine;
dicamba: 3,6-dichloro-2-methoxybenzoic acid and its salts;
glufosinate-ammonium: ammonium (±)-2-amino-4-(hydroxymethylphosphinyl)butanoate;

glyphosate: N-(phosphonomethyl)glycine and its salts;

halosulfuron: 3-chloro-5-[[[[(4,6-dimethoxy-2-pyrimidinyl)amino]carboyl]amino]sulfonyl]-1-methyl-1H-pyrazole-4-carboxylic acid and its methyl ester;

imazamox: 2-[4,5-dihydro-4-methyl-4-(1-methylethyl)-5-oxo-1H-imidazol-2-yl]-5-(methoxymethyl)-3-pyridinecarboxylic acid;

imazapic: 2-[4,5-dihydro-4-methyl-4-(1-methylethyl)-5-oxo-1H-imidazol-2-yl]-5-methyl-3-pyridinecarboxylic acid, its salts and esters;

metolachlor: 2-chloro-N-(2-ethyl-6-methyl-phenyl)-N-(2-methoxy-1-methylethyl)acetamide;

metsulfuron: 2-[[[[(4-methoxy-6-methyl-1,3,5-triazin-2-yl)amino]carbonyl]amino]sulfonyl]benzoic acid and its methyl ester;

oxadiazon: 3-[2,4-dichloro-5-(1-methylethoxy)-phenyl]-5-(1,1-dimethylethyl-1,3,4-oxadiazol-2(3H)-one;

picloram: 4-amino-3,5,6-trichloro-2-pyridine-carboxylic acid and its potassium salt;

sulfentrazone: N-[2,4-dichloro-5-[4-(difluoromethyl)-4,5-dihydro-3-methyl-5-oxo-1H-1,2,4-triazol-1-yl]phenyl]methanesulfonamide;

triclopyr: [(3,5,6-trichloro-2-pyridinyl)oxy]-acetic acid, its esters and salts;

trifloxysulfuron: N-[[(4,6-dimethoxy-2-pyrimidinyl)amino]carbonyl]-3-(2,2,2-trifluoroethoxy)-2-pyridine-sulfonamide; and simazine: 6-chloro-N,N'-diethyl-1,3,5-triazine-2,4-diamine;

optionally in the presence of at least one inorganic or organic base.

* * * * *